United States Patent [19]

Evans

[11] Patent Number: 5,082,485

[45] Date of Patent: Jan. 21, 1992

[54] TREATMENT AND PREVENTION FOR OAK WILT DISEASE OR DECLINE

[76] Inventor: David W. Evans, 603 Mill Run, Kerrville, Tex. 78028

[21] Appl. No.: 253,790

[22] Filed: Oct. 5, 1988

Related U.S. Application Data

[63] Continuation-in-part of Ser. No. 150,692, Jan. 29, 1988, abandoned.

[51] Int. Cl.$^5$ .................. A01N 59/02; A01N 33/18
[52] U.S. Cl. .............................................. 71/3; 71/54; 514/86; 514/345; 514/396; 514/741; 424/704
[58] Field of Search ................ 71/3, 54; 514/86, 741, 514/396, 345; 424/704

[56] References Cited

U.S. PATENT DOCUMENTS

| | | | |
|---|---|---|---|
| 2,299,917 | 10/1942 | Minger et al. | 424/704 |
| 3,632,328 | 6/1972 | Gaskin et al. | 71/3 |
| 4,381,194 | 4/1983 | Dellicolli et al. | 71/65 |
| 4,497,646 | 2/1985 | Rubio | 71/3 |

Primary Examiner—Richard L. Raymond
Assistant Examiner—B. Bembenick
Attorney, Agent, or Firm—William E. Shull

[57] ABSTRACT

Disclosed are compositions and methods of treating oak wilt, decline, or other fungus-induced diseases of trees. A mixture is applied to the root system comprising sulfur and pentachloronitrobenzene or pentachlorophenol as its active ingredients, and optionally other ingredients such as a wetting agent, nitrogen, an insecticide, and a nutrient source. It is preferable to simultaneously treat the bark and crown of the tree with a composition which includes a fungicide and an insecticide. Other ingredients, such as a wetting agent or a fungicide/nutrient, can also be present in the Bark & Crown Composition.

21 Claims, No Drawings

TREATMENT AND PREVENTION FOR OAK WILT DISEASE OR DECLINE

RELATED APPLICATION

This application is a continuation-in-part of application Ser. No. 150,692, filed Jan. 29, 1988, (abandoned) entitled "Composition and Method for Treating Oak Wilt Disease." I claim priority to that filing date.

FIELD OF THE INVENTION

The invention relates to a composition and method for treating the disease known as oak wilt or decline, wherein a mixture which has sulfur and pentachloronitrobenzene or pentachlorophenol as its active ingredients is applied to the roots of an infected tree and, preferably, an insecticide/fungicide composition is applied to its bark and the crown.

BACKGROUND OF THE INVENTION

Oak wilt, or decline, is an infectious disease caused by the fungus Ascomycete Ceratocystis Fagacearum. Its pathogenicity arises because it enters and clogs the vascular system of the tree's roots, trunk and limbs so that it cannot carry the water and nutrients necessary to survival of the tree. During the summer when the disease is most virulent, a live oak may lose all its leaves within thirty days of infection. Most will die within six months to two years. The more susceptible Spanish oaks often die seven to thirty days after infection.

At present, oak wilt disease has reached epidemic proportions in many counties in Texas. It is also present in trees in Minnesota, Pennsylvania and South Carolina. There is every reason to think that the disease will continue to spread, and will eventually infect trees in every state and in other countries as well.

One of the first symptoms of oak wilt is veinal necrosis of the leaves—the leaf dies and turns brown along the veins but remains alive and green elsewhere. Later, the leaves show greater degrees of necrosis. Defoliation usually follows quickly. Trees that are not killed outright by the disease may be weakened to the point where they are susceptible to other pathogens. Some trees may remain in a defoliated state for months or even years.

The fungus quite often spreads locally from tree to tree through rootgrafts and common root systems, i.e., where roots of different trees merge and grow together. It can also be spread through human activity, such as through the use on healthy trees of infected tree pruning equipment. When an infected tree is pruned, fungal spores can remain on and be carried by pruning equipment to a healthy tree. The spores are effectively "injected" directly into the healthy tree's vascular system when pruning cuts are made in its limbs.

Insects can spread the fungus over long distances. Infection of distant trees by insect vectors is particularly likely in trees where fungal mats are formed. Fungal mats are conglomerations of fungus which are typically observed in the Texas red oak. They usually form under cool, moist conditions. The conglomeration acts to push bark away from the tree wood leaving access for insects to the interior of the tree. The sweet odor of the fungal mat actually attracts insects to the interior of the tree where they contact the fungus. Insects then will often carry fungal spores on their bodies to wounds and pruning cuts of healthy trees, thereby infecting them.

It is also likely that birds, rodents, and squirrels carry spores from infected to uninfected trees. Woodpeckers, which bore into the tree, and insect borers such as the Texas Longhorn Borer, are also believed to be culprits, since they come into contact with the vascular systems of both infected and uninfected trees.

Firewood also plays an important role in the spread of the fungus, in that it may harbor insects which spread spores. Insects often spend the winter in piles of firewood and if the wood is infected, will emerge in the spring carrying oak wilt spores. The effect of firewood is particularly noteworthy because it is often transported great distances by humans, thereby leading to the spread of the disease to new areas.

Although several methods have been proposed in the past for combating the spread of the disease, the experts agree that there is no known cure for oak wilt. See Texas Weekly Magazine pp. 6–9 (May 25, 1986) (quoting Dr. D. Appel); R. F. Billings & R. S. Cameron, "Texas Forest Service Forest Pest Suppression Project: Oak Wilt," pp. 27–32 (September 1987) (proposing a method for controlling the spread of the disease).

One method in particular has been recommended for controlling tree-to-tree infection. A trench two to three feet deep, or as deep as the majority of the lateral roots, is dug around the infected trees. Where there is a group of infected trees, a trench is dug around the entire group. The trench is designed to create a barrier to prevent root-to-root infection. As a further precaution it has been recommended that infected trees within the trenched area be uprooted, and that any Texas red oaks—in which fungal mats can form—be burned immediately. As an alternative to trenching, severing the roots chemically with the soil fumigant Vapam has been proposed.

Severing root systems with either method, of course, does nothing to prevent new infections by vectors such as insects, rodents, birds, or squirrels. Moreover, Vapam has not proved effective in field trials conducted in Texas. See R. F. Billings & R. S. Cameron, "Texas Forest Service Forest Pest Suppression Project: Oak Wilt," p. 31 (September 1987).

A more drastic method of control is to kill infected trees with silvicides. This method is less desirable, however, because it not only kills the "patient," but also can kill healthy trees in the area where the silvicides are applied. Silvicides can be absorbed through the root systems.

Any of these prior art methods, coupled with other common sense measures such as thoroughly cleaning pruning equipment, avoiding transport of infected firewood, and avoiding transplanting infected trees, can be somewhat effective in controlling, or at least slowing, the spread of the disease. However, all of these prior art control methods suffer from two serious disadvantages—none can entirely stop the spread of the disease, and none offers a cure for infected trees. It is clear that a more effective treatment is needed to halt the spread of this menace to the great oak trees.

SUMMARY OF THE INVENTION

In a method of treating oak wilt, a mixture is applied to the root system of infected trees preferably comprising sulfur, pentachloronitrobenzene and optionally other ingredients such as a wetting agent, nitrogen, and an insecticide (hereinafter the "Fungicidal Mixture.") It is also possible to substitute pentachlorophenol for pentachloronitrobenzene.

Sulfur, pentachlorophenol, and pentachloronitrobenzene are fungicides. Pentachlorophenol and pentachloronitrobenzene are very effectively absorbed by the tree to kill fungus. Sulfur leaches into the soil more slowly and forms a barrier against fungal infection. The wetting agent acts to keep the composition in suspension and also to increase absorption through the root system. The insecticide is useful to kill insects, particularly fire ants, which burrow around the base of the tree and can infect trees. The nitrogen is designed as a nutrient for the tree, which may be in a weakened state due to the infection.

It is also preferred to simultaneously treat the bark and crown of infected trees with a composition (the "Bark & Crown Composition") which is a mixture of a fungicide (most preferably pentachloronitrobenzene) and an insecticide. Other ingredients, such as wetting agents or nutrients, can also be added to the Bark & Crown Composition.

It should also be noted that the *Ascomycete Ceratocystis Fagacearum* fungus may be able to infect trees other than oaks. The methods and compositions of this invention are believed to be useful in treating fungus-induced diseases in other types of trees. For example, the fungus has been known to attack poplar and sycamore trees.

DESCRIPTION OF THE PREFERRED EMBODIMENTS

(i) The Fungicidal Mixture

The Fungicidal Mixture can contain any of a number of additional components provided that the essential ones—sulfur and either pentachloronitrobenzene or pentachlorophenol—are present. Pentachlorophenol can be toxic to the tree. Therefore, there is an upper limit of concentration of about 16 fluid ounces (hereinafter "ounces" means "fluid ounces") per 100 gallons of mixture. The preferred composition has 4-6 ounces per 100 gallons. It is believed that less than one ounce of pentachlorophenol per 100 gallons would not be effective. The preferred concentration of pentachloronitrobenzene is about 8 ounces per 100 gallons and the upper limit of concentration of pentachloronitrobenzene is about 16 ounces per 100 gallons.

The sulfur can be applied in the form of a wettable sulfur powder (such as one, for example, manufactured by Chemical Enterprises, Inc.), but is preferably applied as part of a liquid fertilizer containing 12% nitrogen and 26% sulfur or "12-0-0-26" fertilizer (such as one, for example, manufactured by Texas Sulphur Products Company), or 20% nitrogen and 46% sulfur ("20-0-0-46" fertilizer). If a wettable sulfur powder is used, the range of concentrations may be from about 20 to about 50 pounds of wettable sulfur powder per 100 gallons of mixture. Since there is no nitrogen in wettable sulfur powder, the sulfur content of the Fungicidal Mixture can be greater using wettable sulfur rather than the combination of sulfur and nitrogen in 12-0-0-26 or 20-0-0-46 fertilizer, since there is no concern with burning the surrounding grass or ground cover with the nitrogen. In the summer the 12-0-0-26 fertilizer is preferably in a fairly small concentration—about 20 pounds (less than 2 gallons) per 100 gallons of total mixture. This small concentration helps avoid burning the grass and ground cover around the tree. In the spring or fall when it is usually cooler and there is more rainfall, the concentration can be 22 to 55 pounds (2-5 gallons) per 100 gallons of mixture. Further, when the pH of the soil is greater than 6.0, more sulfur can be tolerated without damage to grass and ground cover. When applying the 20-0-0-46 fertilizer, the above concentrations for 12-0-0-26 fertilizer can be reduced in proportion to the increased percentage of sulfur in the 20-0-0-46 fertilizer.

The Fungicidal Mixture can also include other nutrients such as the micronutrient composition "FEAST" (TM) (manufactured by Conklin Company, Inc.). This composition acts with the fertilizer in providing nutrients the tree needs for recovery. It is preferably present in a concentration of about 8 ounces per 100 gallons of Fungicidal Mixture.

The Fungicidal Mixture preferably contains an insecticide to kill and repel insects, especially fire ants. Dursban 50W (manufactured by Dow Chemical Company) and Diazinon AG500 (manufactured by Chevron Chemical Company) are two preferred insecticides. The Fungicidal Mixture also preferably includes a wetting agent, for example, WEX or Kombind (both manufactured by Conklin Company, Inc.).

Quantities of Fungicidal Mixture can be applied to the point where the ground is saturated. However, it is preferable to apply 3-5 gallons per diameter inch of tree. This amount can vary, however, with the type of tree being treated. For example, some smaller trees might have to be treated with heavier dosages than some larger trees because the smaller trees may be partly obstructed by the larger trees in the area. The amount applied can also vary with the ground conditions around the roots. This is because the Fungicidal Mixture is designed to form a protective barrier or layer, and where the soil is less porous than normal, this can only be accomplished by increasing the amount applied.

The Fungicidal Mixture can be applied with any method of ground surface application, such as pouring, injecting or spraying around the tree base. It is preferable to inject it into the ground around the tree, either in a one-time application or continuously through dripping, so that it can penetrate the ground more completely. Penetration is desired so that the Fungicidal Mixture can form an underground barrier against the spread of fungus through the root system, and, where an insecticide is included, can also protect against burrowing insects and ants.

It is most preferable that the highest concentration of Fungicidal Mixture be applied about five feet beyond the drip line of the tree (the outermost edge of the branches), since that is where the heaviest concentration of feeder roots to absorb it is located.

The recommended frequency of application is two to three times per year, with applications spaced at about four to six month intervals. The only upper limit on the frequency of application is that too many may damage grass and ground cover. In general, about five to six applications should be applied in order to effect a cure and to create a sufficient barrier against re-infection. However, further applications can be applied if desired.

To determine the minimum number of applications, the tree should be monitored after each application to determine how it is progressing. If it appears completely cured, further treatments may be unnecessary. However, the advantage of further applications is that they allow a build-up of fungicides (sulfur and pentachlorophenol or pentachloronitrobenzene) in the vascular system, and are believed to help prevent re-infection. In addition, the efficacy of the Fungicidal Mixture tends to decrease over time, and new applications offset this effect. Thus, multiple applications are generally desired, irrespective of a tree's rate of response to treatment.

The Fungicidal Mixture is made by simply mixing and/or agitating the ingredients. If the sulfur is in the form of wettable sulfur powder, the mixture must be highly agitated.

Examples of preferred embodiments of the Fungicidal Mixture are set forth below.

EXAMPLE I

Each 50 gallons of Fungicidal Mixture, specially adapted for application in the spring or fall, contains the following ingredients in about the following proportions:

- 2.0 gallons of 12-0-0-26 fertilizer, or 1.4 gallons of 20-0-0-46 fertilizer;
- 8.0 ounces of Dursban 50W;
- 2.0 ounces of pentachlorophenol or pentachloronitrobenzene;
- 4.0 to 6.0 ounces of WEX; and
- the remainder being water.

It is sometimes desirable to separately apply iron chelates, for example, Sequestrum (manufactured by Ciba-Geigy, Inc.), around the tree. These serve as nutrients for the recovering tree, and can be applied in virtually any concentration. However, they are preferably applied by mixing 32 ounces of Sequestrum with 50 to 100 gallons of water, and then spraying the mixture on the ground around the infected tree. This Sequestrum mixture could also be applied to the bark and crown of the tree for enhancement of the nutrient effect.

EXAMPLE II

Each 50 gallons of Fungicidal Mixture, specifically adapted for use during the hot and dry climate of summer, contains the following ingredients in about the following proportions:

- 1.0 gallon of 12-0-0-26 fertilizer, or 0.7 gallon of 20-0-0-46 fertilizer;
- 4.0 ounces of pentachlorophenol or pentachloronitrobenzene;
- 4.0 ounces of WEX;
- 3.0 ounces of Diazinon AG500 or 4.0 ounces of Dursban 50W; and
- the remainder being water.

Once again, it may be desirable to apply a Sequestrum mixture as in Example I.

It is noted that one-half as much fertilizer is used in the Example II mixture as in Example I. Variations of the amount of fertilizer are made in accordance with the climate and time of year, as discussed above, and with the soil conditions. Greater amounts of fertilizer help the natural micronutrients in the soil function more effectively, and therefore more is desired in the winter and when soil is otherwise poor in nutrient value. The upper limit on the fertilizer concentration is that which damages the grass and ground cover.

EXAMPLE III

Each 50 gallons of Fungicidal Mixture contains the following ingredients in about the following proportions:

- 4.0 ounces of pentachloronitrobenzene;
- 1.0 ounce of WEX;
- 2.0 ounces of Kombind;
- 3.0 ounces of Diazinon AG500 or 4.0 ounces of Dursban 50W;
- 4.0 ounces of FEAST;
- ½ gallon of 12-0-0-26 fertilizer.

The above composition was found to be very effective in treating oak wilt disease, when used together with the Bark & Crown composition of Example VII below.

(ii) The Bark & Crown Composition

A Bark & Crown Composition can be applied separately or together with application of the Fungicidal Mixture. The Bark & Crown Composition includes a fungicide, for example, Benlate (manufactured by E. I. DuPont de Nemours & Co., Inc.) or Kocide 101 (manufactured by Kocide Chemical Co.). It further includes an insecticide, for example Dursban 50W or Diazinon AG500. Optionally, it can include pentachloronitrobenzene and/or pentachlorophenol, which helps increase absorption of the active ingredients through the crown and bark and also repels insect vectors, such as borers.

The preferred concentration of Benlate is about ½-2 pounds per 100 gallons of Bark & Crown Composition. For Kocide 101, it is about 3-9 pounds per 100 gallons. In general, these ingredients should be applied in accordance with manufacturers' or label instructions.

The Dursban 50W is preferably used in a concentration of about 16 ounces per 100 gallons of composition. Dursban 50W can be toxic to the tree, and therefore 16 ounces per 100 gallons is also about the maximum concentration. The Diazinon AG500 is preferably used in a concentration of about 6-8 ounces per 100 gallons of composition, with an upper limit of 16 ounces per 100 gallons. The upper limit arises because Diazinon AG500 can also be toxic.

The upper limit of pentachlorophenol in the Bark & Crown Composition, if it is present, is about 8 ounces per 100 gallons. Concentrations larger than this may cause defoliation. The preferred concentration is about 2-4 ounces per 100 gallons. The preferred concentration of pentachloronitrobenzene in the Bark & Crown Composition is about 8 ounces per 100 gallons, with an upper limit of about 16 ounces per 100 gallons.

The Bark & Crown Composition is intended to enhance the efficacy of the Fungicidal Mixture by adding further fungicide to the vascular system, which aids in treatment and also helps prevent re-infection after treatment. The added fungicides in Bark & Crown Composition also kill fungus on the tree surface and thereby help prevent transmission of surface fungus from an infected tree to an uninfected tree. These fungicides also help prevent fungal transmission from the tree's surface into its vascular system where it can do real damage. In the absence of fungicides, where fungus is present on the tree's surface, this surface-to-interior transmission of fungus can be accomplished by a vector such as a woodpecker or a borer.

Kocide 101, which is one of the above-mentioned surface fungicides, also acts to reduce the ball moss which frequently accumulates on trees which are weakened from infection. Including Kocide 101 in the Bark & Crown Composition is preferable when the accumulation of moss is relatively heavy.

The insecticides in the Bark & Crown Composition kill insects and borers to prevent them from infecting other trees, or re-infecting the vascular system of the tree being treated.

The Bark & Crown Composition can also include other ingredients, such as a wetting agent, e.g., WEX or Kombind. WEX or Kombind increases penetration of the fungicides, and also acts as a spreader/sticker which sticks the active ingredients to the tree's leaves or bark. The preferred concentration of WEX is about 1 pint per 100 gallons of composition, with upper and lower limits being those amounts which do not accomplish the desired purpose. Kombind is preferably present at a concentration of about 4 ounces per 100 gallons, with upper and lower limits as for WEX.

Sequestrum, a fungicide/nutrient, which aids trees in a weakened state and is particularly effective in fighting "black patch" fungus, can also be included in the Bark & Crown Composition. The preferred concentration of Sequestrum is about 32 ounces per 100 gallons of composition, with a lower limit being that which does not function effectively.

The Bark & Crown Composition is made by simply mixing and agitating together the ingredients. It can be applied with any method of surface application and is preferably applied with high pressure spraying to the trunk and crown of the tree.

The amount applied varies from about 10 gallons per diameter inch of tree, if there is heavy ball moss, and otherwise is preferably about 3-4 gallons per diameter inch of tree. The preferred time and frequency of application of the Bark & Crown Composition are the same as for the Fungicidal Mixture. However, it could be applied more or less frequently depending upon the amount of rainfall. Greater rainfall increases dissipation and dissolution, and the composition should be applied more frequently to remain on the surface and perform its function.

Specific examples of preferred embodiments of the Bark & Crown Composition are set forth below.

EXAMPLE IV

Each 100 gallons of Bark & Crown Composition, specially adapted for fighting heavy ball moss on diseased trees, includes approximately the following:
6 pounds of Kocide 101;
½ pound of Benlate;
12.0 ounces of Dursban 50W;
4.0 ounces of WEX; and
the remainder being water.

It may be desirable to spray the tree's bark and crown with the mixture of Sequestrum as set forth in Examples I and II. This is done in order to get nutrients into the tree through the leaves and bark. Further, Sequestrum acts as a fungicide and provides a coating on the tree's surface, which can help protect against black patch fungus.

EXAMPLE V

Each 100 gallons of Bark & Crown Composition useful in combatting the oak wilt fungus, includes approximately the following:
½ pound of Benlate;
4.0 ounces of Diazinon AG500;
4.0 to 8.0 ounces of WEX; and
the remainder being water.

EXAMPLE VI 50 gallons of Bark & Crown Composition useful in combatting the oak wilt fungus, includes approximately the following:
3.0 pounds of Kocide 101;
4.0 ounces of Dursban 50W;
2.0 ounces of pentachlorophenol or pentachloronitrobenzene;
1.0 pound of Benlate; and
the remainder being water.

EXAMPLE VII

Each 50 gallons of Bark & Crown Composition, particularly useful in combatting the oak wilt fungus, includes approximately the following:
4.0 ounces of Benlate;
3.0 ounces of Diazinon AG500 or 4.0 ounces of Dursban 50W;
1.0 ounce of WEX or Saturall (a wetting agent manufactured by the Conklin Company, Inc.);
4.0 ounces of pentachloronitrobenzene;
2.0 ounces of Kombind.

This formula was found very effective in reviving diseased trees when used together with the composition of Example III above.

(iii) Results

Some representative results obtained with treating trees as described above were as follows.

I.

A Primary Fungicidal Mixture which did not contain pentachlorophenol or pentachloronitrobenzene was applied in April, 1987, to 160 trees. This Primary Fungicidal Mixture included approximately the following for each 100 gallons of composition:
50 pounds of wettable sulfur powder (manufactured by Chemical Enterprises, Inc.);
½ pound of Benlate;
8.0 ounces of Diazinon AG500;
4.0 to 8.0 ounces of WEX;
the remainder being water.

The Bark & Crown Composition applied in conjunction with this Primary Fungicidal Mixture did not contain any Sequestrum or WEX. This Bark & Crown Composition included the following for each 100 gallons of composition:
2.0 pounds of Benlate;
1.0 ounce of Dursban 50W;
the remainder being water.

For those trees which showed heavy accumulation of ball moss, Kocide 101, in a concentration of 6 pounds per 100 gallons, was used either together with Benlate, or by itself.

About 85% of the trees treated responded, but did not appear to recover fully.

In October 1987, these same 160 trees were treated a second time, this time with a Fungicidal Mixture which included pentachlorophenol. All the trees, even the ones which had not responded when initially treated with the Primary Fungicidal Mixture, responded well. However, many still had some lingering symptoms of oak wilt.

In June 1988, these same 160 trees, many of which still had some symptoms of oak wilt, were sprayed with the compositions of Examples III and VII. These compositions include pentachloronitrobenzene as the fungicide rather than pentachlorophenol. These 160 trees all showed a marked improvement within 30 days, including more rapid foliage growth and greener leaf coloration. Virtually no symptoms of oak wilt were present in any of these 160 trees following the June 1988 treatment.

These results indicate that the addition of pentachlorophenol to the composition makes it more effective in treating oak wilt than when it is not present. Further, these results show that using pentachloronitrobenzene rather than pentachlorophenol makes the treatment even more effective. The results under headings II and III below further demonstrate the effectiveness of using pentachloronitrobenzene in the composition as a treatment for oak wilt.

II.

In October 1987, it was noted that 15 trees which were in close proximity to one another each showed symptoms of oak wilt. Eight of these trees were treated with the compositions of Examples III and VII, and seven were not treated at all. The untreated trees died. However, the treated trees showed dramatic improvement so that within about 30 days, all symptoms of oak wilt had disappeared.

III.

In July 1988, it was observed that eight trees in close proximity to one another had lost much of their foliage and were nearly dead. The owner of the property was preparing to cut these trees down. Instead, they were treated with the compositions of Examples III and VII and showed rapid improvement. Within one month, all symptoms of oak wilt had disappeared, and all trees had new foliage and leaves with a deep green color.

IV.

In March 1987, 42 trees were treated with the Fungicidal Mixture of Example II containing pentachlorophenol and not pentachloronitrobenzene, and what was essentially the Bark & Crown Composition of Example IV, with the difference being that the latter contained 4.0 ounces of pentachlorophenol, 1.0 pound of Benlate, and no Kocide 101. The results are shown in Table I.

TABLE I

| Trees Treated | Trees Recovered | Treatment Number | Treatment Interval | Date of First Treatment |
|---|---|---|---|---|
| 42 | 42 | 2 | 6 mos. | 3/87 |

All of the trees treated appeared to have recovered substantially within 6 months of the first treatment.

V.

In March of 1987, four trees were each treated with about 25 gallons of a Fungicidal Mixture which included the following approximate proportions for each 100 gallons:
- 4.0 ounces of pentachlorophenol;
- 22 pounds (2 gallons) of 12-0-0-26 fertilizer;
- the remainder being water.

These trees were also treated with a Bark & Crown Composition which included about the following proportions for each 100 gallons of composition:
- 4.0 ounces of WEX;
- 1.0 pound of Benlate;
- 16 ounces of 50W Dursban;
- the remainder being water.

The results of these treatments are summarized below in Table II.

VI.

On Mar. 20, 1987, two trees were each treated with about 75 gallons of a Fungicidal Mixture which included approximately the following proportions for each 100 gallons of composition:
- 4.0 ounces of pentachlorophenol;
- 25 pounds of wettable sulfur powder;
- 20 ounces of Benlate;
- 4.0 ounces of WEX;
- 12 pounds of 20% nitrogen fertilizer (manufactured by Texas Sulphur Products Company);
- the remainder being water.

These two trees were also treated with a Bark & Crown Composition which included approximately the following for each 100 gallons of composition:
- 8.0 ounces of Sequestrum
- 8.0 ounces of WEX;
- 1.0 pound of Benlate;
- 8.0 ounces of Diazinon AG500;
- the remainder being water.

By Sept. 1, 1987 —six months later—neither of these trees appeared to show any symptoms.

VII.

On May 19, 1987, 50 healthy trees were treated as a prophylactic measure against oak wilt. About 15 gallons of the following Fungicidal Mixture, which included approximately the following proportions for each 100 gallons of composition, was applied to each tree:
- 4.0 ounces of pentachlorophenol;
- 1.0 gallon of 12-0-0-26 fertilizer;
- 50 pounds of wettable sulfur powder;
- the remainder being water.

Each tree was also treated with about 15 gallons of a Bark & Crown Composition which included approximately the following for each 100 gallons of composition:
- 32.0 ounces of Sequestrum;
- 1.0 pound of Benlate;
- 2.0 ounces of 50W Dursban;
- the remainder being water.

By Sept. 1, 1987 —less than four months after the first application—none of the trees appeared to show any disease symptoms; moreover, all had sprouted dark green leaves indicating vigor and good health. There was a moderate to heavy infestation of oak wilt disease about one quarter of a mile away from these trees. The proximity of these infected trees, and the lack of infection of the treated trees, demonstrates the effectiveness of the treatment as a prophylactic.

It should be understood that the examples, compositions, mixtures, ingredients and methods described herein are exemplary only and not intended as limiting, and that the scope of protection is limited only by the claims which follow and includes all equivalents of the subject matter of the claims.

What is claimed is:

1. A fungicidal mixture designed to be applied around the base of a tree for treating oak wilt disease or decline caused by the fungus *Ascomycete Ceratocystis Fagacea-*

TABLE II

| Trees Treated | Trees Recovered | Treatment Number | Treatment Interval | Date of 1st Treatment | Date(s) of Examination |
|---|---|---|---|---|---|
| 4 | 4 | 2 | 6 mos. | March, 1987 | June 1987 Sept. 1987 |

*rum* in trees, comprising the ingredients sulfur and pentachloronitrobenzene, each ingredient being present in an amount effective to treat said disease.

2. The mixture of claim 1 further including an effective amount of a wetting agent and an insecticide.

3. The mixture of claim 2 further including an effective amount of a nitrogen source.

4. The mixture of claim 3 further including an effective amount of a nutrient source.

5. The mixture of claim 3 wherein the wetting agent is WEX or Kombind or Saturall, the nitrogen and sulfur are in the form of 12-0-0-26 or 20-0-0-46 fertilizer, or both, or a combination of fertilizer and wettable sulfur powder, and the insecticide is Dursban 50W or Diazinon AG500.

6. The mixture of claim 4 wherein the nutrient source is Sequestrum or FEAST.

7. A fungicidal mixture for treating oak wilt disease or decline caused by the fungus *Ascomycete Ceratocystis Fagacearum* wherein for each 100 gallons of mixture, there are the following proportions of ingredients:
   20 to 55 pounds of 12-0-0-26 fertilizer or 12 to 33 pounds of 20-0-0-46 fertilizer;
   4.0 to 16.0 ounces of pentachloronitrobenzene;
   2.0 to 12.0 ounces of WEX; and
   the remainder being water.

8. The mixture of claim 7 further including 8.0 to 16.0 ounces of Dursban 50W or about 6.0 ounces of Diazinon AG500.

9. A method of treating oak wilt disease or decline caused by the fungus *Ascomycete Ceratocystis Fagacearum* in trees comprising applying the mixture of any of claims 1 to 8 around the base of an infected tree.

10. A method of treating oak wilt disease or decline caused by the fungus *Ascomycete Ceratocystis Fagacearum* in trees comprising applying the mixture of claim 1 around the base of an infected tree, and separately applying an iron chelate/water composition around the base of the tree, or to the bark and crown thereof.

11. The method of claim 10 wherein the tree treated is an oak tree and the disease is oak wilt or decline caused by the fungus *Ascomycete Ceratocystis Fagacearum*.

12. The method of claim 11 wherein about three to five gallons per diameter inch of tree of the mixture is applied, and the majority is concentrated about five feet past the drip line of the tree.

13. The method of claim 12 wherein the mixture is applied at least six times at about four to six month intervals.

14. A composition for treating the bark and crown portions of an oak wilt disease or decline infected tree for use in conjunction with an oak wilt disease or decline treatment mixture which is applied to the base of the tree and which includes sulfur and pentachloronitrobenzene, said composition comprising a fungicide and an insecticide.

15. The composition of claim 14 wherein the fungicide is Benlate, Kocide 101, pentachloronitrobenzene or pentachlorophenol, and the insecticide is Dursban 50W or Diazinon AG500.

16. The composition of claim 15 further including a wetting agent and a fungicide/nutrient.

17. The composition of claim 16 wherein the wetting agent is WEX or Kombind and the fungicide/nutrient is Sequestrum.

18. The composition of claim 15 including the following proportions of the ingredients for each 100 gallons of composition:
   ½ pound to 2 pounds of Benlate;
   3.0 to 9.0 pounds of Kocide 101;
   8.0 to 16.0 ounces of Dursban 50W or 4.0 to 16.0 ounces of Diazinon AG500;
   2.0 to 16.0 ounces of WEX; and
   the remainder being water.

19. The composition of claim 15 including the following proportions of the ingredients for each 100 gallons of composition:
   4.0 to 16.0 ounces of pentachloronitrobenzene;
   8.0 to 16.0 ounces of Dursban 50W or 4.0 to 16.0 ounces of Diazinon AG 500;
   ½ pound to 2.0 pounds of Benlate;
   2.0 to 4.0 ounces of Kombind; and
   2.0 to 16.0 ounces of WEX.

20. A Fungicidal Mixture designed to be applied around the base of a tree for treating oak wilt or decline, comprising the following ingredients for each 100 gallons of mixture:
   8.0 ounces of pentachloronitrobenzene;
   6.0 ounces of Diazinon AG500;
   1.0 gallon of 12-0-0-26 fertilizer;
   2.0 ounces of WEX;
   4.0 ounces of Kombind; and
   8.0 ounces of FEAST.

21. A Bark & Crown Composition for use in conjunction with the mixture of claim 20 comprising the following ingredients in the following proportions for each 100 gallons of composition:
   8.0 ounces of pentachloronitrobenzene;
   6.0 ounces of Diazinon AG500;
   ½ pound of Benlate;
   4.0 ounces of Kombind; and
   2.0 ounces of WEX.

* * * * *